United States Patent [19]

Zondler et al.

[11] 4,182,832
[45] Jan. 8, 1980

[54] CURABLE COMPOSITION CONTAINING 1,4-DIAMINOBUTANE DERIVATIVES

[75] Inventors: Helmut Zondler, Bottmingen; Roland Moser; Thaddeus Audykowski, both of Basel, all of Switzerland

[73] Assignee: Ciba-Geigy Corporation, Ardsley, N.Y.

[21] Appl. No.: 950,339

[22] Filed: Oct. 11, 1978

Related U.S. Application Data

[62] Division of Ser. No. 856,952, Dec. 2, 1977, abandoned.

[30] Foreign Application Priority Data

Dec. 10, 1976 [CH] Switzerland .................. 15572/76

[51] Int. Cl.² ........................................... C08G 59/50
[52] U.S. Cl. ............................ 528/103; 260/570.5 P; 528/124; 528/341; 528/407; 525/507
[58] Field of Search .............. 528/124, 135, 341, 407; 528/103

[56] References Cited

U.S. PATENT DOCUMENTS 2,951,824  9/1960  Bruin et al. ..................... 260/47
3,763,102  10/1973  Hoffmann et al. ............. 260/47 EN Primary Examiner—Earl A. Nielsen
Attorney, Agent, or Firm—Joseph F. DiPrima

[57] ABSTRACT 1,4-Diaminobutanes of the formula

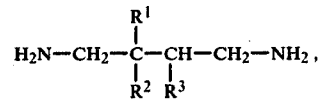

in which $R^1$ is H or —$CH_3$ and $R^2$ and $R^3$ independently of one another are each a radical of the formula

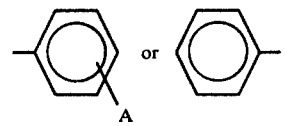

in which A is alkyl having 1 to 3 C atoms, —$OCH_3$, —$N(CH_3)_2$, —Cl or —Br and $R^2$ also is alkyl having 1 to 3 C atoms, are prepared according to the invention by catalytically hydrogenating succinic acid dinitrile of the formula

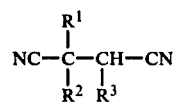

in the presence of acetic anhydride and hydrolyzing the N,N'-diacetyl-1,4-diaminobutanes thus obtained to diamines of the formula I, which are valuable curing agents for epoxide resins.

5 Claims, No Drawings

CURABLE COMPOSITION CONTAINING 1,4-DIAMINOBUTANE DERIVATIVES

This is a divisional of application Ser. No. 856,952, filed on Dec. 2, 1977, and now abandoned.

The invention relates to the preparation of substituted 1,4-diaminobutanes and the use of these compounds as curing agents for epoxide resins.

1,4-Diaminobutanes of this type are mentioned in a publication by H. Schafer in Angew. Chemie 82 (1970) 134 as analysis products obtained in a small amount. In the case of the preparation described in this publication, for example, a mixture of α-methylstyrene, glacial acetic acid and sodium azide is subjected to electrolysis. This results in the formation of 1,4-diazido-2,3-dimethyl-2,3-diphenylbutane, with the evolution of a small amount of nitrogen. After the product has been separated off, it can be catalytically hydrogenated in solution to give 1,4-diamino-2,3-dimethyl-2,3diphenylbutane.

This process of the state of the art, which is intended only for analysis, has, however, the serious disadvantage that azides, which, as is known, are explosive products, are obtained as intermediates. Moreover, the yield from this process is relatively low.

The subject of the present invention is a process for the preparation of 1,4-diaminobutanes of the general formula I $$H_2N-CH_2-\underset{\underset{R^2}{|}}{\overset{\overset{R^1}{|}}{C}}-\underset{\underset{R^3}{|}}{CH}-CH_2-NH_2 \quad (I)$$

in which $R^1$ is H or —$CH_3$ and $R^2$ and $R^3$ independently of one another are each a radical of the formula

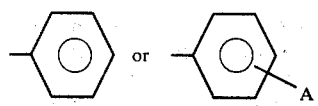

in which A is alkyl having 1 to 3 C atoms, —$OCH_3$, —$N(CH_3)_2$, —Cl or —Br, and $R^2$ is also alkyl having 1 to 3 C atoms, wherein first (a) a succinic acid dinitrile of the formula II $$NC-\underset{\underset{R^2}{|}}{\overset{\overset{R^1}{|}}{C}}-\underset{\underset{R^3}{|}}{CH}-CN \quad (II)$$

is catalytically hydrogenated at temperatures of 20° to 150° C. in the presence of acetic anhydride and, if desired, of additional inert organic solvents, then (b) the N,N'-diacetyl-1,4-diaminobutane obtained by the hydrogenation is subjected, after isolation if desired, to acid or alkaline hydrolysis in an aqueous medium and, finally, (c) the 1,4-diaminobutane of the formula I is isolated either in the form of a salt or, after neutralisation with alkali, in the form of the free base.

A succinic acid dinitrile of the formula II in which $R^1$ is H or —$CH_3$, $R^2$ is one of the radicals

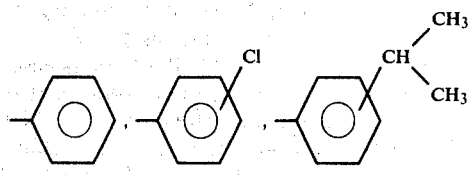

and alkyl having up to 3 C atoms and $R^3$ is one of the radicals

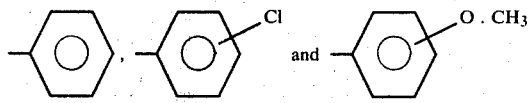

it being possible for $R^2$ and $R^3$ to be identical or different, is preferably used in the process according to the invention.

In a particular embodiment of the process according to the invention, a succinic acid dinitrile of the formula II is employed in which $R^1$ is H and $R^2$ and $R^3$ are each a radical of the formula

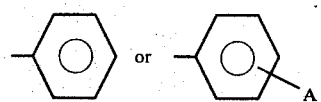

in which A is alkyl having 1 to 3 C atoms, preferably —$CH_3$, or —$OCH_3$, —$N(CH_3)_2$, —Cl or —Br, preferably —Cl.

The substituted N,N'-diacetyl-1,4-diaminobutane obtained as an intermediate in the process according to the invention is of the formula IV $$CH_3.CO.HN-CH_2-\underset{\underset{R^2}{|}}{\overset{\overset{R^1}{|}}{C}}-\underset{\underset{R^3}{|}}{CH}-CH_2-NH.CO.CH_3 \quad (IV)$$

in which $R^1$, $R^2$ and $R^3$ are as defined in formula II. The N,N'-diacetyl derivatives of the formula IV have not yet been described in the literature and are thus valuable starting compounds for the preparation of the 1,4-diaminobutanes of the formula I.

A succinic acid dinitrile of the formula II which is particularly preferentially employed is a succinic acid dinitrile of the formula III

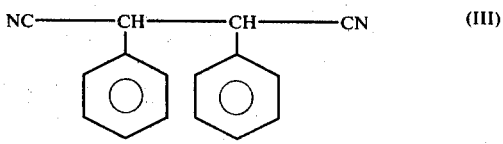

This product can be prepared, for example, by reacting benzaldehyde, benzyl cyanide and sodium cyanide. Other dinitriles of the formula II which are to be used as starting materials for the process according to the invention can also be prepared correspondingly. More precise information on the reaction is to be found in the publication by R. B. Davis in J. Amer. Chem. Soc. 80 (1958) 1,752. All of the dinitriles listed in Table I in this publication can be employed as starting materials for the process according to the invention. Other dinitriles not mentioned in Table I can, of course, also be employed if they correspond to the formula II.

The temperature suitable for the hydrogenation according to stage (a) is in each case dependent on the hydrogenation catalyst used. If Raney nickel or Raney cobalt is used, the reaction conditions are optimum, in respect of the yield, when temperatures of about 90° to 140° C. are used. When known noble metal catalysts, such as platinum, palladium, rhodium or ruthenium, are employed, the reaction can be carried out at lower temperatures, such as, say, at room temperature.

The hydrogenation can be carried out by the methods customary in the laboratory and in industry, either under normal pressure, for example in a duck-shaped shaking vessel, or under pressure in an autoclave.

Additional inert organic solvents which can be used for the hydrogenation are, for example, hydrocarbons or ethers, such as hexane and dioxane, or aromatic compounds, such as toluene or benzene.

The catalytic reduction is as a rule carried out by mixing a solution of the particular succinic acid dinitrile of the formula II in acetic anhydride and, if desired, a solvent with the catalyst and passing hydrogen gas into the reaction mixture. The hydrogenation is continued until no further hydrogen is absorbed. The catalyst is then separated off.

In the second stage (b), the resulting substituted N,N'-diacetyl-1,4-diaminobutane is generally first isolated and then subjected to acid or alkaline hydrolysis. In principle, however, the hydrolysis can also be carried out without separating off the diacetyl compound, i.e. direct in the solution, which has been freed from the catalyst, and is obtained from stage (a). The intermediate is isolated by known processes.

The acylating hydrogenation in the presence of acetic anhydride employed in stage (a) of the process according to the invention is known per se but in the present case ultimately results in solid, substituted 1,4-diaminobutanes which, surprisingly, are outstandingly suitable as curing agents for epoxide resins in respect of pot life, colour stability and stability to aggressive media, especially organic acids and alcohols, and some of which are even superior to some conventional curing agents. This is the case, in particular, for adduct curing agents obtained from the substituted 1,4-diaminobutanes, which can be prepared by the process according to the invention, and liquid polyepoxide compounds.

The 1,4-diaminobutanes of the formula I which can be prepared according to the invention are also particularly suitable for the production of pre-reaction products with epoxide resins (B-stages). For the preparation of such B-stages, as is known, the corresponding epoxide resin is mixed with the curing agent and the mixture is stored either at room temperature for about 1 to 14 days or at slightly elevated temperature (not higher than 60° C.) for one or several hours. The B-stages which form during this storage are used, as is known, inter alia as compression moulding compositions, prepregs for laminates, sintering powders and adhesives. Those based on the 1,4-diaminobutanes of the formula I which can be prepared according to the invention are suprisingly superior to the conventional B-stages which, as is known, contain predominantly aromatic amines as the curing agents. This superiority is particularly surprising because the basic character of the 1,4-diaminobutanes of the formula I is rather that of aliphatic amines. However, as is known, aliphatic amines are unsuitable in practice for the preparation of B-stages.

The invention further also relates to 1,4-diamino-2,3-diphenylbutane, which is characterised in that it has a melting point of 144° to 145° C. and is in the meso form.

The invention further also relates to curable mixtures containing a 1,4-diaminobutane of the formula I and a polyepoxide compound (designated X here) having, on average, more than one epoxide group in the molecule, there being, in the mixtures, 0.5 to 1.5 equivalents of active hydrogen atoms, bonded to nitrogen, in the particular 1,4-diaminobutane per 1 equivalent of epoxide groups in the epoxide compound (X).

A preferred form of the curable mixtures according to the invention comprises those which contain the 1,4-diaminobutane of the formula I in the form of an adduct curing agent (E) having an amine number of 4.0 to 4.7 obtained from the 1,4-diaminobutane of the formula I and a liquid epoxide compound (designated Z here) having, on average, more than one epoxide group in the molecule and, if desired, phenylglycide. In such mixtures there are 0.8 to 1.2 equivalents of active hydrogen atoms bonded to the nitrogen atoms of the adduct curing agent (E) per 1 equivalent of epoxide groups in the epoxide compound (X). Bisphenol A epoxide resins or bisphenol F epoxide resins are preferably employed as liquid epoxide compounds (Z) for the preparation of the adduct curing agents (E). The preparation of the adduct curing agents (E) is preferably effected by warming a mixture of a 1,4-diaminobutane of the formula I, an epoxide compound (Z) and, if desired, phenylglycide (molar ratio: 1.0:0.13:0.2) to temperatures of 120° C. to 200° C.

The adduct curing agent (E) can additionally also contain 5 to 10% by weight, relative to the pure adduct curing agent, of salicylic acid as a reaction accelerator.

The invention further also relates to the B-stages which are stable on storage and have already been described and which are to be regarded as a preferred form of the curable mixtures according to the invention.

Polyepoxide compounds (X) which can be used for the curable mixtures according to the invention are, in particular, those having on average more than one glycidyl group, β-methylglycidyl group or 2,3-epoxycyclopentyl group bonded to a hetero-atom (for example sulphur and preferably oxygen or nitrogen); preferred compounds are bis-(2,3-epoxycyclopentyl) ether; di- or poly-glycidyl ethers of polyhydric aliphatic alcohols, such as 1,4-butanediol, or polyalkylene glycols, such as polypropylene glycols; di- or poly-glycidyl ethers of cycloaliphatic polyols, such as 2,2-bis-(4-hydroxycyclohexyl)-propane; di- or poly-glycidyl ethers of polyhydric phenols, such as resorcinol, bis-(p-hydroxyphenyl)methane, 2,2-bis-(p-hydroxyphenyl)-propane (=diomethane), 2,2-bis-(4'-hydroxy-3',5'-dibromophenyl)-propane, 1,1,2,2-tetrakis-(p-hydroxyphenyl)-ethane or of condensation products of phenols with formaldehyde obtained under acid conditions, such as phenol novolacs and cresol novolacs; di- or poly(β-methylglycidyl) ethers of the abovementioned polyhydric alcohols or polyhydric phenols; polyglycidyl esters of polybasic carboxylic acids, such as phthalic acid, terephthalic acid, $\Delta^4$-tetrahydrophthalic acid and hexahydrophthalic acid; N-glycidyl derivatives of amines, amides and heterocyclic nitrogen bases, such as N,N-diglycidyl-aniline, N,N-diglycidyltoluidine and N,N,N',N'-tetraglycidyl-bis-(p-aminophenyl)-methane; triglycidyl isocyanurate; N,N'-diglycidylethyleneurea;

N,N'-diglycidyl-5,5-dimethyl-hydantoin and N,N'-diglycidyl-5-isopropyl-hydantoin; and N,N'-diglycidyl-5,5-dimethyl-6-isopropyl-5,6-dihydro-uracil.

If desired, active diluents, for example styrene oxide, butyl glycidyl ether, isooctyl glycidyl ether, phenyl glycidyl ether, cresyl glycidyl ether or glycidyl esters of synthetic, highly branched, mainly tertiary aliphatic monocarboxylic acids ("CARDURA E"), can be added to the polyepoxides in order to lower the viscosity.

The curing of the curable mixtures according to the invention to give mouldings and the like is carried out in the temperature range of 20° to 160° C. when the free 1,4-diaminobutanes of the formula I are used. However, if the mixtures contain the described adduct curing agents of the 1,4-diaminobutanes, curing is preferably carried out at temperatures of 5° to 250° C.

In order to shorten the gelling times or curing times, known accelerators for the amine curing reaction, for example monophenols or polyphenols, such as phenol or diomethane, salicyclic acid, tertiary amines or salts of thiocyanic acid, such as NH$_4$SCN, can be added.

Furthermore, conventional modifiers, such as extenders, fillers and reinforcing agents, pigments, dyes, organic solvents, plasticisers, flow control agents, agents for conferring thixotropy, flameproofing agents and mould release agents, can be added to the curable mixtures, according to the invention, of polyepoxide compounds (X) and 1,4-diaminobutanes of the formula (I) or corresponding adduct curing agents in any stage before curing.

The following may be mentioned as examples of extenders, reinforcing agents, fillers and pigments which can be employed in the curable mixtures according to the invention: coal tar, bitumen, liquid coumarone-indene resins, textile fibres, glass fibres, asbestos fibres, boron fibres, carbon fibres, cellulose, polyethylene powders and polypropylene powders; quartz powder; mineral silicates, such as mica, asbestos powder or slate powder; kaolin, aluminium oxide trihydrate, chalk powder, gypsum, antimony trioxide, bentones, silica aerogel ("AEROSIL"), lithopones, baryte, titanium dioxide, carbon black, graphite, oxide colours, such as iron oxide, or metal powders, such as aluminium powder or iron powder.

Suitable organic solvents for modifying the curable mixtures are, for example, toluene, xylene, n-propanol, butyl acetate, acetone, methyl ethyl ketone, diacetone alcohol, ethylene glycol monomethyl ether, ethylene glycol monoethyl ether and ethylene glycol monobutyl ether.

Examples of plasticisers which can be employed for modifying the curable mixtures are dibutyl phthalate, dioctyl phthalate and dinonyl phthalate, tricresyl phosphate, trixylenyl phosphate, diphenoxyethylformal and polypropylene glycols. These plasticisers can also already be constituents of the curing agent, especially of the adduct curing agent. In such cases, the plasticisers are present in a concentration of 25 to 50% by weight, relative to the pure curing agent.

Examples of flow control agents which can be added when the curable mixtures are employed particularly in surface protection are silicones, liquid acrylic resins, cellulose acetobutyrate, polyvinylbutyral, waxes, stearates and the like (some of which are also used as mould release agents).

Particularly for use in the lacquer field, the polyepoxide compounds can furthermore be partially esterified in a known manner with carboxylic acids, such as, in particular, higher unsaturated fatty acids. It is also possible to add other curable synthetic resins, for example phenoplasts or aminoplasts, to such lacquer resin formulations.

The curable mixtures according to the invention can be produced in a conventional manner with the aid of known mixing equipment (stirrers, kneaders, rolls, or, in the case of solid powders, mills or dry mixers).

The curable epoxide resin mixtures according to the invention are employed in particular in the fields of surface protection, the electrical industry, laminating processes and adhesives technology and in the building trade. They can be used in a formulation suited in each case to the particular application, in the unfilled or filled state, if appropriate in the form of solutions or emulsions, as paints, lacquers and solvent-free coatings, as sintering powders, compression moulding compositions, injection moulding formulations, dipping resins, casting resins, impregnating resins, binders and adhesives and as tool resins, laminating resins, sealing and filling compositions, floor covering compositions and binders for mineral aggregates.

(A) Preparation Example

EXAMPLE 1

Precursor: N,N'-Diacetyl-1,4-diamino-2,3-diphenyl-butane 34.9 g (0.15 mol) of 2,3-diphenyl-succinic acid dinitrile are hydrogenated at 120°–125° C. and under a pressure of 120 atmospheres gauge in 200 ml of toluene and 35.3 g (0.36 mol) of acetic anhydride in an autoclave in the presence of 3.5 g of Raney nickel. The absorption of H$_2$ has ceased after 30 minutes and N,N'-diacetyl-1,4-diamino-2,3-phenylbutane crystallises out on cooling. The supernatant solution is decanted off and the residue is boiled with 300 ml of ethanol, whereupon the product dissolves. In order to separate off the catalyst, the mixture is filtered hot and the filtrate is partially concentrated. The product then crystallises out and is filtered off at room temperature, washed with ethanol and dried at 80° C. Yield: 30.5 g; melting point: 221°–222° C. A further 3.4 g of substance are obtained by concentrating, so that the total yield is 33.9 g (69.5% of theory). For analysis, 1 g is recrystallised from 10 ml of ethanol. Yield: 0.8 g; melting point 221°–222° C.

Analysis C$_{20}$H$_{24}$N$_2$O$_2$ (molecular weight=324.41)—Calculated: C 74.04; H 7.46; N 8.64; Found: C 74.11; H 7.58; N 8.68.

The NMR spectrum agrees with the structure.

1,4-Diamino-2,3-diphenylbutane 385.7 g (1.19 mols) of N,N'-diacetyl-2,3-diphenyl-1,4-diaminobutane in 715 ml of 5 N sodium hydroxide solution are heated to 200° C. in an autoclave for 16 hours. After cooling, the mixture is extracted with 1,800 ml of chloroform. Further extraction with 2 times 200 ml of chloroform and concentration of the extracts gives 285.4 g of crude product, which is recrystallised from 2.6 l of benzene. Yield: 258.5 g of 1,4-diamino-2,3-diphenylbutane; melting point: 144°–145° C. A further 15.1 g of substance having a melting point of 144°–145° C. are obtained by concentrating the mother liquor; the total yield is thus 273.6 g (95.7% of theory). For analysis, 1.0 g is recrystallised from 10 ml of benzene. Yield: 0.88 g; melting point: 144°–145° C; meso form.

Analysis $C_{16}H_{20}N_2$ (molecular weight=240.34)—Calculated: C 79.95; H 8.39; N 11.66; Found: C 79.88; H 8.31; N 11.69.

The NMR spectrum agrees with the structure.

EXAMPLE 2

Precursor: N,N'-Diacetyl-1,4-diamino-2-(p-chlorophenyl)-3-(p-methoxyphenyl)-butane.

29.6 g (0.10 mol) of 2-(p-chlorophenyl)-3-(p-methoxyphenyl)-succinic acid dinitrile are hydrogenated for 4 hours at 110° C. and under a pressure of 100 atmospheres gauge in 200 ml of toluene and 25 g (0.24 mol) of acetic anhydride in an autoclave in the presence of 3 g of Raney nickel. The total reaction mixture is then concentrated in a rotary evaporator, the residue is boiled up with 700 ml of ethanol and the Raney nickel is filtered off. After concentrating the filtrate to 200 ml, the product crystallises out. After filtering off, washing and drying, 19.0 g (48.8% of theory) of a substance having a melting point of 235°–238° C. are obtained. The filtrate is completely evaporated in a rotary evaporator; recrystallisation of the residue from 100 ml of ethanol gives a further 2.3 g of product having a melting point of 232°–236° C.

Total yield: 21.3 g (54.7% of theory).

1,4-Diamino-2-(p-chlorophenyl)-3-(p-methoxyphenyl)-butane 21.14 g (0.054 mol) of N,N'-diacetyl-1,4-diamino-2-(p-chlorophenyl)-3-(p-methoxyphenyl)-butane in 80 ml of 15% strength aqueous sodium hydroxide solution are heated to 200° C. in an autoclave for 12 hours. After cooling, the mixture is extracted with chloroform and the organic phase is washed with water and then evaporated in a rotary evaporator. Yield of crude product: 13.2 g (79.6% of theory) of a crystalline product. For purification, this product is recrystallised from 200 ml of cyclohexane, then filtered off, washed with cyclohexane and dried in vacuo at 60° C. Yield: 11.55 g (69.6% of theory); melting point: 124°–127° C.

Analysis $C_{17}H_{21}N_2OCl$ (molecular weight=304.82)—Calculated: C 66.99; H 6.94; N 9.19; Found: C 67.06; H 6.87; N 9.09.

EXAMPLE 3

Precursor: N,N'-Diacetyl-1,4-diamino-2-p-tolyl-3-phenyl-butane.

24.6 g (0.10 mol) of 2-p-tolyl-3-phenyl-succinic acid dinitrile are hydrogenated at 120° C. and under 100 atmospheres gauge in 250 ml of toluene and 31 g (0.30 mol) of acetic anhydride in an autoclave in the presence of 2.5 g of Raney nickel until a constant pressure is reached. The total mixture is concentrated to about 100 ml in a rotary evaporator, 600 ml of ethanol are added, the mixture is heated to the reflux temperature and the catalyst is filtered off hot. After concentrating the filtrate to about 300 ml, the product crystallises out on cooling in a refrigerator. Yield: 18.5 g (54.6% of theory); melting point: 226°–7° C. A further 3.0 g (8.9% of theory) of product having a melting point of 222°–6° C. are obtained by concentrating the mother liquor. Recrystallisation of 0.80 g of the first fraction from 12 ml of ethanol gives 0.49 g of pure product having a melting point of 226°–7° C.

Analysis $C_{21}H_{26}N_2O_2$ (molecular weight=338.45)—Calculated: C 74.53; H 7.74; N 8.28; Found: C 74.39; H 7.71; N 8.49.

1,4-Diamino-2-p-tolyl-3-phenyl-butane 18.6 g of N,N'-diacetyl-1,4-diamino-2-p-tolyl-3-phenyl-butane in 80 ml of 15% strength aqueous sodium hydroxide solution are heated to 200° C. in an autoclave for 16 hours. On concentrating the solution, the amine partially crystallises out. The mixture is extracted 3 times with 50 ml of chloroform and after evaporating the extracts in a rotary evaporator 13.8 g of crystalline crude amine are obtained. Recrystallisation from 110 ml of cyclohexane gives 12.2 g (87.3% of theory) of diamine having a melting point of 112°–14° C.

Analysis $C_{17}H_{22}N_2$ (molecular weight=254.38)—Calculated: C 80.27; H 8.72; N 11.01; Found: C 80.05; H 8.64; N 11.34.

EXAMPLE 4

Precursor: N,N'-Diacetyl-1,4-diamino-2-(p-dimethylaminophenyl)-2-phenyl-butane.

13.4 g of 2-(p-dimethylamino-phenyl)-3-phenyl-succinic acid dinitrile are hydrogenated at 120° C. and under 100 atmospheres gauge in 250 ml of toluene and 15 g of acetic anhydride in an autoclave in the presence of 1.5 g of Raney nickel until constant pressure is reached. The mixture is concentrated to 50 ml, 300 ml of ethanol are added and, after boiling up, the catalyst is filtered off. All of the solvents are then removed in a rotary evaporator and the residue is recrystallised from 60 ml of acetonitrile. 3.1 g of a product having a melting point of 205°–9° C. are obtained in the first fraction. The NMR spectrum is in agreement with the structural formula 1,4-Diamino-2-(p-dimethylamino-phenyl)-3-phenyl-butane 19.1 g of N,N'-diacetyl-1,4-diamino-2-(p-dimethylaminophenyl)-3-phenyl-butane in 80 ml of 15% strength aqueous sodium hydroxide solution are heated to 200° C. in an autoclave for 16 hours. The reaction solution is then concentrated in a rotary evaporator and extracted with chloroform. After removing the chloroform in vacuo, 8.5 g of crystalline crude amine are obtained and this is recrystallised from 35 ml of isopropanol. Yield: 3.8 g of product having a melting point of 145°–146° C. A further 2.0 g of product having a melting point of 145°–146° C. are obtained by concentrating.

Analysis $C_{18}H_{25}N_3$ (molecular weight=283.42)—Calculated: C 76.28; H 8.90; N 14.83; Found: C 76.26; H 8.93; N 14.74.

(B) Use Examples

EXAMPLE I (Casting and adhesive resin)

31.8 g of 1,4-diamino-2,3-diphenylbutane are homogenised, by means of a triple roll mill, together with 100 g of a liquid unmodified epoxide resin (X) which is based on bisphenol A and has an epoxide content of 5.3 equivalent/kg and a viscosity of 10,800 cP/25°, a viscous white suspension being obtained.

The following methods are used to determine the various characteristics:

(a) Determination of the reactivity

Differential thermal analysis is used to determine the reactivity. About 20 mg of the resin/curing agent mixture to be tested are warmed in a small Al crucible in the measuring chamber of a type TA 2000 differential thermoanalyser from Messrs. Mettler (Greifensee, Switzerland) at a heating rate of 4°/minute and the temperature difference between this crucible and an empty crucible warmed at the same time is recorded continuously. The temperatures for the start of reaction, for the maximum reaction rate and for the end of the reaction are read off, as parameters characterising the reactivity, from the curve thus obtained. The area under the curve enables the heat liberated during the reaction to be determined and gives an indication of the completeness of the conversion.

(b) Determination of the Glass Transition Temperature 4 g of the resin/curing agent mixture are, in each case, poured into a thin-walled Al crucible of about 5 cm diameter and completely cured in this crucible (4 hours at 80° C. and 8 hours at 140° C.). A sample is taken from the disc thus obtained in order to determine the glass transition temperature of the crosslinked polymer with the aid of differential thermal analysis. The specific heat changes at the transition point; this change is registered as a turning point in the curve recorded by the DTA apparatus. Conclusions regarding the dimensional stability of the resulting polymer when hot can be drawn from the glass transition temperature.

(c) Determination of the Mechanical and Dielectric Properties of Moulding Materials The resin/curing agent mixture prepared as described above is poured into aluminium moulds, which have been pretreated with mould release agents, in order to produce sheets having dimensions of 135×135×4 mm and 135×135×2 mm and the sheets are cured for 4 hours at 80° C. and 8 hours at 140° C.

The 4 mm thick sheets are used to produce test pieces having dimensions of 60×10×4 mm for determining the flexural strength and deflection according to VSM Standard Specification 77,103, the impact strength according to VSM Standard Specification 77,105 and the increase in weight after storage in water.

The 2 mm thick sheets are used to determine the dielectric properties.

(d) Test to Determine the Suitability as an Adhesive

A small amount of the resin/curing agent mixture is applied, in each case, to the ends of test strips made of anticorodal B which have dimensions of 170×25×1.5 mm and have previously been roughened by grinding and degreased by washing with solvents. In each case, two of these test strips are so adjusted with the aid of a gauge that the ends coated with resin/curing agent mixture overlap by 12 mm. After fixing with a clamp, the adhesive is cured and after cooling the clamp is removed and the tensile shear strength of the glue bond is then tested in a tensile test (DIN 53,183).

(e) Test to Determine the Chemical Stability

A small amount of the resin/curing agent suspension is distributed on a sheet of glass by means of a glass rod so that a uniform film is obtained. The coating obtained after curing is tested to determine its chemical stability by leaving a drop of the particular chemicals on the film for 1 hour. The chemicals are then wiped off and the surface of the film is assessed visually.

The characteristics determined for the various test pieces by the methods mentioned are summarised in Table 1.

(f) Evaluation of the Results

Example I shows that mixtures of 1,4-diamino-2,3-diphenylbutane and epoxide resins are very reactive and give mouldings with good mechanical and electrical properties and a high glass transition temperature. If the mixtures are applied in a thin layer in the form of a solvent-free coating, films are obtained which have very good stability towards solvents and aggressive chemicals in aqueous solution. Mixtures of this type can also readily be used for glue bonds.

Table 1

| (relating to Example I) | | |
|---|---|---|
| System | | 100 parts of epoxide resin based on bisphenol A 31.8 parts of 1,4-diamino-2,3-diphenylbutane |
| Thermal analysis on TA 2000 | $T_S$ | 36° |
| | $T_{RRmax}$ | 102° |
| | $T_E$ | 177° |
| | Enthalpy | 20,815 cal/equivalent of epoxide/amine system |
| Curing | | 4 hours at 80° C. + 8 hours at 140° C. |
| Appearance of the moulding material | | white, opaque |
| Impact strength (cmkg/cm$^2$) | | 5.5 |
| Flexural strength (kg/mm$^2$) | | 9.2 |
| Deflection (mm) | | 3.2 |
| Glass transition temperature (°C.) | | 151 |
| Absorption of H$_2$O, 4 days at room temperature (%) | | 0.29 |
| Absorption of H$_2$O, 1 hour in boiling water (%) | | 0.63 |
| Tensile shear strength (kg/mm$^2$) | | 1.7 |
| Chemical stability towards 5N H$_2$SO$_4$ 5N NaOH H$_2$O acetone Cl-benzene | | no attack of any type detectable |
| Loss factor tan δ | | |
| >1% above | | 79° |
| >5% above | | 104° |
| Dielectric constant ε at 25° C. | | 3.6 |
| Specific volume resistivity 25° (Ω.× cm) | | $4.7 \times 10^{16}$ |

Explanation of the symbols:
$T_{RRmax.}$ = Temperature at the maximum rate of reaction
$T_S$ = Temperature at the start of the reaction
$T_E$ = Temperature at the end of the reaction EXAMPLE II (Solvent-free coating systems)

Preparation of the Adduct Curing Agents

Adduct Curing Agent I According to the Invention 50 g of a liquid epoxide resin (Z) based on bisphenol A and having an epoxide equivalent weight of 168 and a viscosity of about 3,400 cP (25° C.) are mixed together with 180 g of diphenoxyethylformal and 240 g of 1,4-diamino-2,3-diphenylbutane in a three-necked flask and the mixture is heated to 150° C. 30 g of phenylglycide are then added dropwise and the mixture is reacted at 150°–170° C. for 25 minutes. After cooling to about 120° C., 35 g of salicylic acid and melted into the mixture, with stirring. The finished adduct curing agent is discharged at about 50° C. Characteristics: see Table 2

Conventional Adduct Curing Agent II (as comparison)

Based on: 4,4'-diamino-diphenylmethane.

Table 2

(Characteristics of the curing agents according to Example II)

| Curing agent | Viscosity at 25° C. in cP (according to Hoeppler) | Amine number | H equivalent weight | Suitable mixing ratio of epoxide resin to be cured: adduct curing agent |
| --- | --- | --- | --- | --- |
| I | >100,000 | 4.5 | 127 | 100:66 |
| II | 6,700 | 4.5 | 115 | 100:60 |

Production of the Coatings and Testing Thereof

A liquid bisphenol A epoxide resin (X) having a viscosity of 11,300 cP at 25° C. and an epoxide equivalent weight of 194 is mixed with the adduct curing agent I in a weight ratio of 100:66 (mixture I). An analogous mixture is also prepared using the conventional adduct curing agent II (mixture II). In both cases, cleaned, 0.8 mm thick steel sheets are coated to a thickness of 200 μm (thickness of the wet film) with the mixtures I and II. These metal sheets are used to determine the properties in respect of lacquer technology and these properties are compared in Table 3. In order to test the stability towards dilute acetic acid and alcohol, further steel sheets are coated to a layer thickness of 300 μm. The corresponding results are compared in Table 4.

Table 3

(Properties in respect of lacquer technology for mixtures I and II and the coatings produced)

| Mixture | I | II |
| --- | --- | --- |
| Gel time for 100 ml (Tecam apparatus) | >210 mins. | 140 mins. |
| Viscosity of the mixture (25° C.) cP | ~50,000 | 9,000 |
| Time for drying to touch/hours | 7 | 12 |
| Through-curing time/hours | 20 | 15 |
| Appearance of the film 20°/65% relative humidity | good | good |
| Appearance of the film 20°/100% relative humidity | good | good |
| Appearance of the film 5°/45% relative humidity | good | good |
| Hardness (Persoz) seconds/7 days | 320 | 345 |
| Erichsen $^m/m$/7 days | 3–5 | <2 |
| Impact cmkg | 30–40 | ~40 |
| Adhesion on sand-blasted sheet steel | good | moderate |
| Stability to boiling water (6 hours/96° C.) | good | good |
| Curing at 5° C./hours | ~72 | ~72 |

Table 4

(Stability of the coatings towards dilute acetic acid and ethyl alcohol in months
Layer thickness: about 300 μm on sand-blasted sheet steel, curing 10 days)

| Mixture | I | II | III | IV |
| --- | --- | --- | --- | --- |
| Acetic acid, 5% | >6 | >12 | >12 | 1 D |
| Acetic acid, 10% | >6 | >12 | >8 | 1 D |
| Ethanol, 20% | — | >12 | >7 | — |
| Ethanol, 50% | 1–6 A | 7.9 D | <1 D | — |

Legend:
1–6 A signifies: Film attacked, for example softer or formation of bubbles, from 1–6 months
1 D signifies: Film destroyed before 1 month
>6 and >8 signifies: Film intact after 6 and 8 months respectively (test continued)
Mixture III containing: curing agent III = adduct (associate) of 4,4'-diamino-3,3-dimethyl-dicyclohexylmethane and nonylphenol
Mixture IV containing: curing agent IV = adduct (associate) of trimethylhexamethylenediamine and nonylphenol.

Evaluation of the Results

If the processing characteristics, which are very important industrially, and the properties in respect of lacquer technology which are achieved with the coatings are first compared with the aid of Table 3, the curable mixture I containing the adduct curing agent I based on 1,4-diamino-2,3-diphenylbutane has a longer pot life (of >210 minutes) compared with the mixture II containing the adduct curing agent II based on 4,4'-diamino-diphenylmethane and this facilitates easy processing by hand with a brush and roller, for which there is a great demand in practice.

Some of the other properties in respect of lacquer technology of such coatings are superior to the properties of coatings which contain curing agents based on conventional aromatic amines. The colour stability of the novel adduct curing agent I is significantly better and this makes it possible, for example, to produce white-pigmented coatings.

In respect of the stability to highly aggressive media such as dilute organic acids (5% strength and 10% strength acetic acid) and also 20% and 50% ethyl alcohol, which are a factor determining the quality in the foodstuffs sector, the novel adduct curing agent I shows up very well when compared with the curing agent based on 4,4'-diaminodiphenylmethane and is distinctly superior to the other conventional curing agents based on aliphatic and cycloaliphatic polyamines (comparison mixtures III and IV, Table 4).

EXAMPLE III (Pre-reaction product which is stable on storage; B-stage)

The resin/curing agent mixture described in Example I and a suspension prepared from 100 parts by weight of the same epoxide resin (X) and 26.2 parts by weight of 4,4'-diaminodiphenylmethane, which is intended to enable a comparison to be made with the state of the art, are stored at room temperature (RT) and their reactivity and their softening range are checked at specific intervals. Two different experimental methods are used for this purpose:

(a) Determination of the gel time at 120° C. on a thermostatically controlled hot-plate and (b) Determination of the reactivity using the Differential Thermoanalyser already described above.

In addition to changes in the temperatures for the melting point, the start of reaction and the reaction maximum, the determination of the heat of reaction further liberated during complete curing of the pre-reaction products in particular enables an assessment to be made of the degree of conversion before and after storage of the pre-reaction product.

The values determined for the two systems by the methods mentioned are summarised in Table 5.

Table 5

| System | (B-stages) Bisphenol A epoxide resin/1,4-diamino-2,3-diphenylbutane | | | | | | | Bisphenol A epoxide resin/4,4'-diamino-diphenylmethane | | | | | | |
|---|---|---|---|---|---|---|---|---|---|---|---|---|---|---|
| Storage time at RT in days | no storage | 1 | 3 | 10 | 30 | 60 | 90 | no storage | 1 | 3 | 10 | 30 | 60 | 90 |
| Gel time at 120° C. | 3'30" | 3'30" | 2'25" | 2'15" | 2'15" | 2'15" | 2'15" | 16'30" | 16'30" | 3'30" | 1'55" | 1'30" | 1'15" | 28" |
| Gel time in %, the 100% value corresponding to the value with no storage | 100 | 100 | 69 | 64 | 64 | 64 | 64 | 100 | 89.9 | 21.2 | 11.6 | 9.1 | 7.5 | 2.8 |
| Thermal analysis on TA 2000 melting point (°C.) | viscous | → | → | → | highly viscous | → | very highly viscous | — | — | 45 | 55 | 59 | 61 | 64 |
| $T_S$ (°C.) | 46 | 47 | 54 | 55 | 56 | 56 | 58 | 49 | 43 | 55 | 62 | 68 | 68 | 71 |
| $T_{RRmax}$ (°C.) | 104 | 102 | 101 | 101 | 100 | 100 | 107 | 140 | 126 | 125 | 125 | 126 | 125 | 126 |
| cal/equivalent | 20,815 | 15,540 | 13,005 | 13,330 | 13,550 | 14,125 | 12,360 | 25,960 | 15,650 | 9,480 | 7,885 | 6,810 | 7,240 | 6,480 |
| Conversion effected (%) | — | 25.3 | 37.5 | 36 | 35 | 32 | 40.6 | — | 39.7 | 63.5 | 69.4 | 73.8 | 72.1 | 76.0 |

Explanation of the symbols:
$T_S$ = Temperature at the start of the reaction
$T_{RRmax}$ = Temperature at the maximum rate of reaction

Evaluation of the Results

According to Example III it is surprisingly possible by simply grinding the solid amine of the formula I prepared according to the invention with the liquid epoxide resin (X) to obtain pastes which, although they show a distinct rise in viscosity after storing for a period of days, can still be applied as a paste even after 90 days and have virtually the same gel time as after storage for 3 days at room temperature. This is the more surprising because diaminodiphenylmethane, which because of its chemical structure is considerably less reactive, under the same conditions results in a paste which becomes solid after only 3 days storage at room temperature.

Examples IV and V

In accordance with Example I, 34.3 g of 1,4-diamino-2-p-tolyl-3-phenylbutane and 41.2 g of 1,4-diamino-2-(p-chlorophenyl)-3-(p-methoxyphenyl)-butane are each homogenised, by means of a triple roll mill, with 100 g of the same epoxide resin based on bisphenol A, a viscous suspension being obtained. The characteristics of the mouldings and B-stage resins prepared therefrom are given in Table 6 and 7.

Table 6

| System | | 100 parts of epoxide resin based on bisphenol A 34.3 parts of 1,4-diamino-2-p-tolyl-3-phenylbutane | 100 parts of epoxide resin based on bisphenol A 41.2 parts of 1,4-diamino-2-(p-chlorophenyl)-3-(p-methoxyphenyl)-butane |
|---|---|---|---|
| Thermal analysis on TA 2000 | $T_S$ | 44° | 43° |
| | $T_{RRmax.}$ | 100° | 100° |
| | $T_E$ | 206° | 195° |
| | Enthalpy | 21,370 cal/equivalent of epoxide/amine system | 20,600 cal/equivalent of epoxide/amine system |
| Curing | | 4 hours at 80° + 8 hours at 140° | 4 hours at 80° + 8 hours at 140° |
| Glass transition temperature (°C.) | | 130 | 115 |
| Tensile shear strength (kg/mm²) | | 1.5 | 2.3 |
| Chemical stability towards 5N H₂SO₄, 5N NaOH, H₂O, acetone, Cl-benzene | | no attack of any type discernible | no attack of any type discernible |

Explanation of the symbols:
$T_{RRmax.}$ = Temperature at the maximum rate of reaction
$T_S$ = Temperature at the start of reaction
$T_E$ = Temperature at the end of reaction Table 7

| System | (B-stages) Bisphenol A epoxide resin/ 1,4-diamino-2-p-tolyl-3-phenylbutane | Bisphenol A epoxide resin/ 1,4-diamino-2-(p-chlorophenyl)-3-(p-methoxyphenyl)-butane |
|---|---|---|
| Storage time at RT | no | no |

Table 7-continued

| | (B-stages) | | | | | | |
|---|---|---|---|---|---|---|---|
| | Bisphenol A epoxide resin 1,4-diamino-2-p-tolyl-3-phenylbutane | | | Bisphenol A epoxide resin/ 1,4-diamino-2-(p-chlorophenyl)-3-(p-methoxyphenyl)-butane | | | |
| System | | | | | | | |
| in days | storage | 3 | 10 | storage | 5 | 10 | 30 |
| Gel time at 120° C. | 3'5" | 50" | 50" | 3'45" | 1' | 45" | 30" |
| Gel time in %, the 100% value corresponding to the value with no storage | 100 | 27 | 27 | 100 | 27 | 20 | 13 |
| Thermal analysis on TA 2000 | | | | | | | |
| melting point (°C.) | viscous | solid | solid | viscous | solid | solid | solid |
| $T_S$ (°C.) | 44 | 55 | 58 | 43 | 52 | 53 | 58 |
| $T_{RRmax}$ | 100 | 104 | 104 | 100 | 109 | 109 | 110 |
| cal/equivalent | 21,370 | 9,200 | 8,210 | 20,580 | 7,795 | 7,705 | 7,765 |
| Conversion effected (%) | — | 57 | 62 | — | 62.1 | 62.6 | 62.3 |

Explanation of the symbols:
$T_S$ = Temperature at the start of the reaction
$T_{RRmax}$ = Temperature at the maximum rate of reaction Since they have a lower degree of conversion, the solid and fusible B-stage resins obtained from the amines prepared according to the invention and the liquid epoxide resin based on bisphenol A can be applied more easily than the B-stage resins obtained from diaminodiphenylmethane and the same epoxide resin under the same conditions.

What is claimed is:

1. A curable mixture comprising (a) a 1,4-diaminobutane, of the formula I

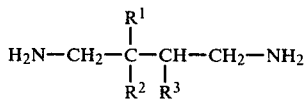

in which $R^1$ is H or —$CH_3$ and $R^2$ and $R^3$ independently of one another are each denote a radical of the formula

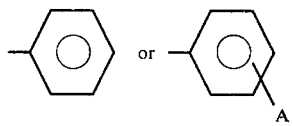

in which A is alkyl having 1 to 3 C atoms, —$OCH_3$, —$N(CH_3)_2$, —Cl or —Br, and $R^2$ is also alkyl having 1 to 3 C atoms, and (b) a polyepoxide compound (X) having, on average, more than one epoxide group in the molecule, there being, in the mixture, 0.5 to 1.5 equivalents of active hydrogen atoms, bonded to nitrogen, in the particular 1,4-diaminobutane per 1 equivalent of epoxide groups in the epoxide compound (X).

2. A mixture according to claim 1 which comprises a 1,4-diaminobutane of the formula I in which $R^1$ is H or —$CH_3$, $R^2$ is one of the radicals

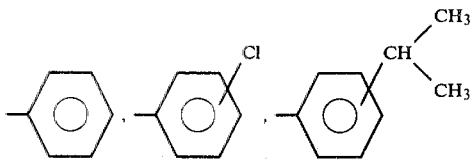

or alkyl having up to 3 C atoms and $R^3$ is one of the radicals

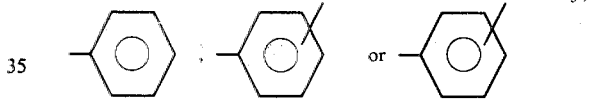

it being possible for $R^2$ and $R^3$ to be identical or different.

3. A mixture according to claim 1 which comprises, as the 1,4-diaminobutane of the formula I, 1,4-diamino-2,3-diphenylbutane which has a melting point of 144° to 145° C. and is in the meso form.

4. A mixture according to claim 1 which comprises the 1,4-diaminobutane of the formula I in the form of an adduct curing agent (E) having an amine number of 4.0 to 4.7, said adduct being obtained from the 1,4-diaminobutane of the formula I and a liquid epoxide compound (Z) having, on average, more than one epoxide group per molecule, and optionally phenylglycide, there being, in the mixture, 0.8 to 1.2 equivalents of active hydrogen atoms bonded to the nitrogen atoms of the adduct curing agent (E) per 1 equivalent of epoxide groups in the epoxide compound (X).

5. A mixture according to claim 4 which comprises an adduct curing agent (E) which has been prepared by reacting the 1,4-diaminobutane of the formula I with the epoxide compound (Z) and optionally with phenylglycide, at a temperature of 120° to 200° C., the 1,4-diaminobutane, the epoxide compound (Z) and the phenylglycide having been in a molar ratio of 1.0:0.13:0.2 in the reaction mixture.

* * * * *